United States Patent
Ohkubo et al.

(10) Patent No.: US 10,590,049 B2
(45) Date of Patent: Mar. 17, 2020

(54) METHOD FOR PRODUCING TETRAFLUOROPROPENE

(71) Applicant: DAIKIN INDUSTRIES, LTD., Osaka (JP)

(72) Inventors: Shun Ohkubo, Osaka (JP); Takashi Usui, Osaka (JP); Takehiro Chaki, Osaka (JP); Daisuke Karube, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 16/074,524

(22) PCT Filed: Feb. 3, 2017

(86) PCT No.: PCT/JP2017/004076
§ 371 (c)(1),
(2) Date: Aug. 1, 2018

(87) PCT Pub. No.: WO2017/135443
PCT Pub. Date: Aug. 10, 2017

(65) Prior Publication Data
US 2019/0039975 A1    Feb. 7, 2019

(30) Foreign Application Priority Data
Feb. 3, 2016  (JP) ................. 2016-018619

(51) Int. Cl.
*C07C 17/20*     (2006.01)
*C07C 21/18*     (2006.01)
*C07C 17/15*     (2006.01)
*C07B 61/00*     (2006.01)

(52) U.S. Cl.
CPC ............ *C07C 17/206* (2013.01); *C07C 17/15* (2013.01); *C07C 17/20* (2013.01); *C07C 21/18* (2013.01); *C07B 61/00* (2013.01)

(58) Field of Classification Search
CPC ........ C07C 17/206; C07C 21/18; C07C 17/25
See application file for complete search history.

(56) References Cited

U.S. PATENT DOCUMENTS

| | | | |
|---|---|---|---|
| 9,856,191 B2 * | 1/2018 | Ohkubo | ............ B01J 23/6522 |
| 2011/0160497 A1 | 6/2011 | Deur-Bert et al. | |
| 2012/0330073 A1 * | 12/2012 | Karube | ................... C07C 17/21 |
| | | | 570/156 |
| 2014/0303412 A1 * | 10/2014 | Karube | ................. C07C 17/206 |
| | | | 570/160 |
| 2016/0052841 A1 | 2/2016 | Karube et al. | |
| 2017/0210686 A1 | 7/2017 | Pigamo et al. | |

FOREIGN PATENT DOCUMENTS

| | | |
|---|---|---|
| JP | 2014-500858 | 1/2014 |
| JP | 2014-224089 | 12/2014 |
| WO | 2010/123154 | 10/2010 |
| WO | 2012/052797 | 4/2012 |
| WO | 2012/098421 | 7/2012 |
| WO | 2012/098422 | 7/2012 |
| WO | 2014/174918 | 10/2014 |
| WO | 2016/001515 | 1/2016 |

OTHER PUBLICATIONS

International Search Report dated Mar. 21, 2017 in International (PCT) Application No. PCT/JP2017/004076.
Extended European Search Report dated Jul. 24, 2019 in corresponding European Application No. 17747594.4.

* cited by examiner

*Primary Examiner* — Jafar F Parsa
(74) *Attorney, Agent, or Firm* — Wenderoth, Lind & Ponack, L.L.P.

(57) ABSTRACT

The present invention provides a method for producing tetrafluoropropene represented by formula (1) by bringing monochlorotrifluoropropene represented by formula (2) into contact with anhydrous hydrogen fluoride in the presence of a catalyst, the method being capable of maintaining the conversion of the starting material and the selectivity for the target product within an excellent range, while reducing degradation of the catalyst to maintain the reaction for a long time. The invention specifically relates to a method for producing tetrafluoropropene represented by formula (1) $CF_3CX=CHX$ wherein Xs are different from each other and represent H or F, including the step of bringing an organic substance containing monochlorotrifluoropropene represented by formula (2) $CF_3CY=CHY$ wherein Ys are different from each other and represent H or Cl into contact with anhydrous hydrogen fluoride in the presence of a catalyst in a reactor, wherein the amount of the anhydrous hydrogen fluoride supplied to the reactor is 30 moles or more per mole of the organic substance supplied to the reactor.

10 Claims, No Drawings

METHOD FOR PRODUCING TETRAFLUOROPROPENE

TECHNICAL FIELD

The present invention relates to a method for producing tetrafluoropropene.

BACKGROUND ART

Tetrafluoropropene represented by formula (1) $CF_3CX=CHX$ wherein Xs are different from each other and represent H or F is known as a useful compound, such as for refrigerants, solvents, and foaming agents. Of the tetrafluoropropene represented by formula (1), 2,3,3,3-tetrafluoropropene (HFO-1234yf) represented by formula $CF_3CF=CH_2$ and 1,3,3,3-tetrafluoropropene (HFO-1234ze) represented by formula $CF_3CH=CHF$ have shown promise as refrigerants with a low global warming potential.

As a method for producing tetrafluoropropene represented by formula (1), the following method, for example, is known: the method that allows monochlorotrifluoropropene represented by formula (2) $CF_3CY=CHY$ wherein Ys are different from each other and represent H or Cl (a starting material) to react with a fluorinating agent, such as anhydrous hydrogen fluoride, in the presence of a catalyst (see PTL 1).

Tetrafluoropropene represented by formula (1) is produced, for example, by a gas-phase continuous reaction of monochlorotrifluoropropene represented by formula (2) in the presence of a catalyst. However, this method is known to cause degradation of the catalyst when the reaction is maintained for a long time (see PTL 2).

The degradation of the catalyst is believed to be caused by decomposed matter or polymerized products adhering to the catalyst surface that result from decomposition or polymerization of monochlorotrifluoropropene used as a starting material, by-products generated in the reaction, and the like.

To reduce this degradation of the catalyst, for example, a method is reported in which the decomposed matter or polymerized products are removed by supplying an oxidizing agent, such as oxygen gas or chlorine gas, to a reactor (see PTL 1 and 3).

However, the use of oxygen gas for reducing the degradation of a catalyst requires the supply of a large amount of oxygen relative to the amount of the supplied starting material, and the inhibitory effect on catalyst degradation is also not considered to be satisfactory. Additionally, a lower selectivity of the target product may result in the use of chlorine gas for reducing the degradation of a catalyst, because chlorine gas, due to its high reactivity, may react with the starting material compound and the like.

Because of the problems described above, there is demand for a method for producing tetrafluoropropene represented by formula (1) by reacting monochlorotrifluoropropene represented by formula (2) as a starting material with anhydrous hydrogen fluoride in the presence of a catalyst, the method being capable of maintaining the conversion of the starting material and the selectivity of the target product within an excellent range, while reducing degradation of the catalyst to maintain the reaction for a long time.

CITATION LIST

Patent Literature

PTL 1: JP2014-500858A
PTL 2: WO2014/174918
PTL 3: WO2010/123154

SUMMARY OF INVENTION

Technical Problem

The present invention was made in view of the problems of prior art described above, and an object of the invention is to provide a method for producing tetrafluoropropene represented by formula (1) by reacting monochlorotrifluoropropene represented by formula (2) with anhydrous hydrogen fluoride in the presence of a catalyst, the method being capable of maintaining the conversion of the starting material and the selectivity of the target product within an excellent range, while reducing degradation of the catalyst to maintain the reaction for a long time.

Solution to Problem

The present inventors conducted extensive research to achieve the object and, to their surprise, found that in a method for producing tetrafluoropropene represented by formula (1) by reacting monochlorotrifluoropropene represented by formula (2) with anhydrous hydrogen fluoride in the presence of a catalyst in a reactor, supplying the anhydrous hydrogen fluoride to the reactor in an amount of 30 moles or more, per mole of an organic substance containing the monochlorotrifluoropropene supplied to the reactor enables the conversion of the starting material and the selectivity of the target product to be maintained within an excellent range, while reducing the degradation of the catalyst to maintain the reaction for a long time. The inventors conducted further research based on these findings and completed the present invention.

Specifically, the present invention includes the subject matter described in the following items as representative examples.

Item 1.

A method for producing tetrafluoropropene represented by formula (1) $CF_3CX=CHX$
wherein Xs are different from each other and represent H or F,
the method comprising the step of bringing an organic substance containing monochlorotrifluoropropene represented by formula (2) $CF_3CY=CHY$ wherein Ys are different from each other and represent H or Cl into contact with anhydrous hydrogen fluoride in the presence of a catalyst in a reactor,
wherein the amount of the anhydrous hydrogen fluoride supplied to the reactor is 30 moles or more per mole of the organic substance supplied to the reactor.

Item 2.

The production method according to Item 1, wherein the amount of the anhydrous hydrogen fluoride supplied to the reactor is 30 to 100 moles per mole of the organic substance supplied to the reactor.

Item 3.

The production method according to Item 1 or 2, wherein the catalyst is a fluorination catalyst.

Item 4.

The production method according to any one of Items 1 to 3, comprising supplying an oxidizing agent to the reactor.

Item 5.

The production method according to Item 4, wherein the amount of the oxidizing agent supplied to the reactor is 0.0001 to 0.5 moles per mole of the organic substance supplied to the reactor.

Item 6.

The production method according to Item 4 or 5, wherein the oxidizing agent is oxygen.

Advantageous Effects of Invention

The present invention enables, in a method for producing tetrafluoropropene represented by formula (1) by reacting monochlorotrifluoropropene represented by formula (2) with anhydrous hydrogen fluoride in the presence of a catalyst, the conversion of the starting material and the selectivity of the target product to be maintained within an excellent range, while reducing the degradation of the catalyst. As a result, the reaction can be maintained for a long time.

DESCRIPTION OF EMBODIMENTS

The following describes the present invention in more detail.

The present invention relates to a method for producing tetrafluoropropene represented by formula (1) $CF_3CX=CHX$ wherein Xs are different from each other and represent H or F. In this specification, the method may be referred to as "the production method of the present invention."

The tetrafluoropropene represented by formula (1) is specifically 2,3,3,3-tetrafluoropropene (HFO-1234yf) represented by formula $CF_3CF=CH_2$, or 1,3,3,3-tetrafluoropropene (HFO-1234ze) represented by formula $CF_3CH=CHF$.

The production method of the present invention comprises the step of bringing an organic substance containing monochlorotrifluoropropene represented by formula (2) $CF_3CY=CHY$ wherein Ys are different from each other and represent H or Cl into contact with anhydrous hydrogen fluoride in the presence of a catalyst in a reactor. In this specification, this step may be referred to as "reaction step." The reaction step allows the monochlorotrifluoropropene represented by formula (2) contained in the organic substance to react with anhydrous hydrogen fluoride, thereby giving tetrafluoropropene represented by formula (1), which is the target product.

The monochlorotrifluoropropene represented by formula (2) is specifically 2-chloro-3,3,3-trifluoropropene (HCFO-1233xf) represented by formula $CF_3CCl=CH_2$, or 1-chloro-3,3,3-trifluoropropene (HCFO-1233zd) represented by formula $CF_3CH=CHCl$. In the production method of the present invention, either HCFO-1233xf or HCFO-1233zd may be used, or HCFO-1233xf and HCFO-1233zd may be mixed and used.

The use of HCFO-1233xf as the monochlorotrifluoropropene represented by formula (2) gives HFO-1234yf as the tetrafluoropropene represented by formula (1), while the use of HCFO-1233zd as the monochlorotrifluoropropene represented by formula (2) gives HFO-1234ze as the tetrafluoropropene represented by formula (1). The use of a mixture of HCFO-1233xf and HCFO-1233zd as the monochlorotrifluoropropene represented by formula (2) gives HFO-1234yf and HFO-1234ze as the tetrafluoropropene represented by formula (1).

In this specification, the "organic substance containing monochlorotrifluoropropene represented by formula (2)" refers to not only monochlorotrifluoropropene represented by formula (2) supplied to the reactor as a starting material, but also a mixture containing, in addition to the monochlorotrifluoropropene represented by formula (2) supplied to the reactor as a starting material, other organic compounds such as unreacted starting materials and by-products generated by the reaction that are recovered from the reactor and supplied to the reactor again (i.e., recycled). Examples of the by-products generated by the reaction that can be contained in the organic substance include 1,1,1,2,2-pentafluoropropane (HFC-245cb) represented by formula $CH_3CF_2CF_3$, 1,1,1,3,3-pentafluoropropane (HFC-245fa) represented by formula $CHF_2CH_2CF_3$, HFO-1234ze, and HCFO-1233zd, when HCFO-1233xf is used as a starting material; and HFC-245fa, when HCFO-1233zd is used as a starting material. When the organic substance is a mixture containing other organic compounds in addition to the monochlorotrifluoropropene represented by formula (2), the monochlorotrifluoropropene represented by formula (2) is typically contained in the organic substance in an amount of 70% or more, and preferably 85% or more, while other organic compounds are typically contained in an amount of less than 30%, and preferably less than 15%.

The catalyst for use in the reaction step may be a known catalyst that exhibits activity in the reaction for generating tetrafluoropropene represented by formula (1) from monochlorotrifluoropropene represented by formula (2) and anhydrous hydrogen fluoride. Examples of such a catalyst include fluorination catalysts. Examples of fluorination catalysts include metal oxide, such as chromium oxide, aluminum oxide, magnesium oxide, and cobalt oxide; metal oxyfluoride, such as chromium oxyfluoride, fluorinated alumina, magnesium oxyfluoride, cobalt oxyfluoride, and nickel oxyfluoride; and metal halide, such as aluminum fluoride, magnesium fluoride, nickel fluoride, niobium fluoride, tantalum fluoride, antimony fluoride, barium fluoride, antimony chloride, chlorofluoroantimony, and chlorofluorobarium. These fluorination catalysts may be used singly or in a combination of two or more. When two or more fluorination catalysts are mixed for use, examples of the combination of fluorination catalysts include the combination of chromium oxide and niobium fluoride, the combination of chromium oxide and magnesium fluoride, the combination of chromium oxyfluoride and fluorinated alumina, the combination of chromium oxyfluoride and cobalt oxyfluoride, and the combination of chromium oxyfluoride, nickel fluoride, and aluminum fluoride. The shape of the catalyst is not particularly limited, and a catalyst with a known shape, such as powder or pellets, may be used.

The catalyst for use may be supported by a carrier. The carrier is not particularly limited, and known carriers used in the technical field to which the present invention pertains may be used. Examples include fluorinated alumina, aluminum fluoride, chromium fluoride, nickel fluoride, activated carbon, fluorinated activated carbon, and graphite carbon. Examples of the combination of a catalyst and a carrier (catalyst/carrier) include alumina/activated carbon, fluorinated alumina/activated carbon, aluminum fluoride/activated carbon, magnesium fluoride/aluminum fluoride, and chromium oxyfluoride/aluminum fluoride.

The method for placing a catalyst in the reactor is not particularly limited, as long as the catalyst is present such that the starting material sufficiently comes into contact with the catalyst. Examples include a method in which a catalyst is packed in a reactor.

The reactor is not particularly limited, but the reactor for use is preferably made from a material resistant to the corrosive action of hydrogen fluoride used in the reaction step. Examples of the material resistant to the corrosive action of hydrogen fluoride include materials such as Hastelloy, Inconel, and Monel. The reactor for use may be one reactor or two or more reactors. When two or more reactors are used, the reactors may be only one type of reactor or two or more different types of reactor.

The method for bringing the organic substance containing monochlorotrifluoropropene represented by formula (2) into contact with anhydrous hydrogen fluoride is not particularly limited, and, for example, they can be brought into contact with each other by individually supplying them to the reactor in the vapor phase. It is sufficient if the organic substance is in its gas form when coming into contact with anhydrous hydrogen fluoride; before the organic substance is supplied to the reactor, part of or all of the organic compounds contained in the organic substance may be in their liquid form. For instance, when at least one component of an organic compound contained in the organic substance is liquid at room temperature under ordinary pressure, the organic substance containing the organic compound may be vaporized with an evaporator or the like before being supplied to the reactor.

The organic substance containing monochlorotrifluoropropene represented by formula (2) may be supplied to the reactor as is, or supplied to the reactor together with gas inert to the starting material, the catalyst, and the like, when dilution is required, for example, for controlling the reactivity. Examples of the inert gas include nitrogen, helium, and argon.

When the organic substance containing monochlorotrifluoropropene represented by formula (2) is supplied to the reactor together with inert gas, the amount of inert gas is preferably within the range in which unnecessary decreases in reactivity due to dilution do not occur. For example, the amount of inert gas is preferably 10 mol % or less based on the total amount of gas components supplied to the reactor, more specifically, the total amount of the organic substance containing monochlorotrifluoropropene represented by formula (2), anhydrous hydrogen fluoride, and inert gas.

When the reactor has only one supply port, the organic substance containing monochlorotrifluoropropene represented by formula (2) supplied to the reactor as a starting material, before being supplied to the reactor, may be mixed with other organic compounds, such as unreacted starting materials and by-products generated by the reaction that are recovered from the reactor and supplied to the reactor again (i.e., recycled), and the mixture is then supplied to the reactor. When the reactor has two or more supply ports, monochlorotrifluoropropene represented by formula (2) supplied as a starting material and recycled other organic compounds may be separately supplied from different supply ports to the reactor such that a mixture containing monochlorotrifluoropropene represented by formula (2) and other organic compounds is famed in the reactor.

In the reaction step, the reaction temperature is not particularly limited as long as the reaction for generating tetrafluoropropene represented by formula (1) from monochlorotrifluoropropene represented by formula (2) and anhydrous hydrogen fluoride occurs at that temperature, and is, for example, 200 to 450° C., preferably 300 to 400° C., and more preferably 325 to 390° C.

In the reaction step, the pressure inside the reactor is not particularly limited and may be reduced pressure, ordinary pressure, or increased pressure.

In the reaction step, the contact time during which the organic substance containing monochlorotrifluoropropene represented by formula (2) is in contact with anhydrous hydrogen fluoride is not particularly limited. However, an overly short contact time may lead to insufficient conversion of the monochlorotrifluoropropene represented by formula (2) into tetrafluoropropene represented by formula (1), while an overly long contact time may generate an increased amount of undesired by-products in the reaction. Thus, an appropriate contact time can be determined taking into consideration these aspects. For example, the contact time represented by the ratio (W/F$_0$) of the amount of a catalyst packed in the reactor W(g) to the total flow rate of gas supplied to the reactor F$_0$ (flow rate at 0° C. at 0.1 MPa: mL/sec) is preferably about 0.5 to 70 g·sec/mL and more preferably 1 to 50 g·sec/mL. The total flow rate of the gas supplied to the reactor refers to the flow rate determined by adding, when inert gas is used, the flow rate of inert gas to the flow rate of the organic substance containing monochlorotrifluoropropene represented by formula (2) and anhydrous hydrogen fluoride.

A feature of the production method of the present invention is that anhydrous hydrogen fluoride supplied to the reactor is 30 moles or more per mole of the organic substance containing monochlorotrifluoropropene represented by formula (2) supplied to the reactor. When the amount of anhydrous hydrogen fluoride supplied to the reactor is 30 moles or more per mole of the supply amount of the organic substance, degradation of the catalyst is reduced. The phrase "anhydrous hydrogen fluoride supplied to the reactor" refers to not only the anhydrous hydrogen fluoride supplied to the reactor as a starting material but also a mixture of anhydrous hydrogen fluoride supplied to the reactor as a starting material and anhydrous hydrogen fluoride contained in a mixture recovered from the reactor, when the mixture of unreacted starting materials, by-products generated in the reaction, and the like are recovered from the reactor and these are supplied to the reactor again (i.e., recycled). The amount of anhydrous hydrogen fluoride supplied to the reactor is 30 moles or more, preferably 35 moles or more, and more preferably 40 moles or more, per mole of the organic substance supplied to the reactor. When two or more reactors are used, the lower limit (30 moles) means the amount of anhydrous hydrogen fluoride supplied to each reactor, per mole of the organic substance supplied to each reactor.

The upper limit of the amount of anhydrous hydrogen fluoride supplied to the reactor per mole of the organic substance supplied to the reactor is not particularly limited. However, an overly high amount of anhydrous hydrogen fluoride does not provide an inhibitory effect on catalyst degradation in line with the increases in the supply amount of anhydrous hydrogen fluoride. Thus, the amount of anhydrous hydrogen fluoride supplied to the reactor per mole of the organic substance supplied to the reactor is preferably 100 moles or less, more preferably 90 moles or less, still more preferably 80 moles or less, further more preferably 70 moles or less, and particularly preferably 60 moles or less. When two or more reactors are used, the supply amount described above means the amount of anhydrous hydrogen fluoride supplied to each reactor per mole of the organic substance supplied to each reactor.

In other words, the amount of anhydrous hydrogen fluoride supplied to the reactor per mole of the organic substance supplied to the reactor is preferably 30 to 100 moles, more preferably 30 to 90 moles, still more preferably 30 to 80 moles, further more preferably 30 to 70 moles, and particularly preferably 30 to 60 moles. When two or more reactors are used, the numerical ranges described above mean the amount of anhydrous hydrogen fluoride supplied to each reactor per mole of the organic substance supplied to each reactor.

Additionally, the production method of the present invention may comprise supplying an oxidizing agent to the reactor. The oxidizing agent is not particularly limited, as long as the agent is used for inhibiting catalyst degradation. Examples include oxygen, chlorine, ozone, hypochlorous acid, chlorous acid, dinitrogen oxide, and nitrogen oxide. From the standpoint of reducing undesired side reaction between the oxidizing agent and the starting material compounds, the use of oxygen as an oxidizing agent is preferable. When two or more reactors are used, oxidizing agents supplied to the reactors may be different.

The method for supplying the oxidizing agent to the reactor is not particularly limited. Examples include a method in which a gaseous oxidizing agent is supplied to a reactor. The oxidizing agent may be supplied alone to a reactor, or with an entrained organic substance containing monochlorotrifluoropropene represented by formula (2).

The amount of the oxidizing agent supplied to the reactor per mole of the organic substance supplied to the reactor is not particularly limited, and is, for example, 0.0001 to 0.5 moles, preferably 0.001 to 0.5 moles, and more preferably 0.001 to 0.2 moles. When two or more reactors are used, these numerical ranges refer to the amount of the oxidizing agent supplied to each reactor per mole of the organic substance supplied to each reactor. When two or more reactors are used, there may be a reactor to which the oxidizing agent is supplied and another reactor to which the oxidizing agent is not supplied.

The production method of the present invention may comprise, in addition to the reaction step described above, the step of separating tetrafluoropropene represented by formula (1), which is the reaction product obtained from the reactor outlet over the reaction step, from organic compounds including unreacted starting materials such as monochlorotrifluoropropene represented by formula (2) and anhydrous hydrogen fluoride and by-products generated in the reaction to recover tetrafluoropropene represented by formula (1). In this specification, this step may be referred to as "separation and recovery step." For this separation and recovery step, the method for separating tetrafluoropropene represented by formula (1), which is the reaction product, from organic compounds including unreacted starting materials such as monochlorotrifluoropropene represented by formula (2) and anhydrous hydrogen fluoride and by-products generated in the reaction to recover tetrafluoropropene represented by formula (1) is not particularly limited, and a known method may be used. Examples include distillation. Because of this step, tetrafluoropropene represented by formula (1), which is the target product, can be obtained.

The production method of the present invention may also comprise, in addition to the reaction step and the separation and recovery step described above, the step of supplying the organic compounds including unreacted starting materials such as monochlorotrifluoropropene represented by formula (2) and anhydrous hydrogen fluoride and by-products generated in the reaction that are separated in the separation and recovery step to the reactor again for recycle use (i.e., recycling). Supplying the organic compounds such as unreacted starting materials and by-products generated in the reaction to the reactor again in this way enables the reaction to continuously proceed.

EXAMPLES

The following describes the present invention in more detail with reference to Examples and Comparative Examples. However, the present invention is not limited to the following Examples.

Example 1

20 g of a chromium oxide catalyst (specific surface area: 12 $cm^2/g$) was packed into a corrosion-resistant-metal-tubular reactor. Subsequently, the temperature of the reactor was increased to 365° C., and hydrogen fluoride gas (flow rate: 120 Nml/min) was supplied to the reactor and maintained for 1 hour. Thereafter, HCFO-1233xf gas was supplied to this reactor (flow rate: 3.0 Nml/min). At the time point of about 3 hours after the supply of HCFO-1233xf gas started, the first sample of gas flowing out of the reactor outlet was collected and analyzed by gas chromatography. Subsequently, at the time point of about 70 hours after the supply of HCFO-1233xf gas started, a sample of gas flowing out of the reactor outlet was collected again and analyzed by gas chromatography. The change in conversion of HCFO-1233xf from the first sample was then confirmed.

Example 2

In the same manner as in Example 1, 20 g of a chromium oxide catalyst (specific surface area: 12 $cm^2/g$) was packed into a corrosion-resistant-metal-tubular reactor. Subsequently, the temperature of the reactor was increased to 365° C., and hydrogen fluoride gas (flow rate: 120 Nml/min) and oxygen gas (flow rate: 0.30 Nml/min) were supplied to the reactor and maintained for 1 hour. Thereafter, HCFO-1233xf gas was supplied to this reactor (flow rate: 3.0 Nml/min). In the same manner as in Example 1, at the time point of about 3 hours after the supply of HCFO-1233xf gas started, the first sample of gas flowing out of the reactor outlet was collected and analyzed by gas chromatography. Subsequently, at the time point of about 70 hours after the supply of HCFO-1233xf gas started, a sample of gas flowing out of the reactor outlet was collected again and analyzed by gas chromatography. The change in conversion of HCFO-1233xf from the first sample was then confirmed.

Example 3

An experiment was performed in the same manner as in Example 2 except that the flow rate of HCFO-1233xf was changed to 4.0 Nml/min, and the flow rate of oxygen gas was changed to 0.40 Nml/min.

Comparative Example 1

In the same manner as in Example 1, 20 g of a chromium oxide catalyst (specific surface area: 12 $cm^2/g$) was packed into a corrosion-resistant-metal-tubular reactor. Subsequently, the temperature of the reactor was increased to 365° C., and hydrogen fluoride gas (flow rate: 120 Nml/min) was supplied to the reactor and maintained for 1 hour. Thereafter, HCFO-1233xf gas was supplied to this reactor (flow rate: 12 Nml/min). In the same manner as in Example 1, at the time point of about 3 hours after the supply of HCFO-1233xf gas started, the first sample of gas flowing out of the reactor outlet was collected and analyzed by gas chromatography. Subsequently, at the time point of about 30 hours after the supply of HCFO-1233xf gas started, a sample of gas flowing out of the reactor outlet was collected again and analyzed by gas chromatography. The change in conversion of HCFO-1233xf from the first sample was then confirmed.

Comparative Example 2

An experiment was performed in the same manner as in Example 2 except that the flow rate of HCFO-1233xf was changed to 12 Nml/min, and the flow rate of oxygen gas was changed to 1.2 Nml/min.

Comparative Example 3

An experiment was performed in the same manner as in Example 2 except that the flow rate of HCFO-1233xf was changed to 8.0 Nml/min, and the flow rate of oxygen gas was changed to 0.80 Nml/min.

Table 1 below shows the results of Examples 1 to 3 and Comparative Examples 1 to 3. In Table 1, "hydrogen fluoride/starting material (molar ratio)" refers to the molar amount of supplied anhydrous hydrogen fluoride per mole of HCFO-1233xf supplied to the reactor; "catalyst degradation inhibitor/starting material (molar ratio)" refers to the molar amount of a supplied catalyst degradation inhibitor per mole of HCFO-1233xf supplied to the reactor; "1233xf conversion" refers to the ratio of the total molar amount of compounds other than HCFO-1233xf contained in the gas flowing out of the reactor outlet to the molar amount of HCFO-1233xf supplied to the reactor (GC %); and "selectivity" refers to the ratio of the molar amount of a specific compound (HFO-1234yf or HFC-245cb) contained in the gas flowing out of the reactor outlet to the total molar amount of compounds other than HCFO-1233xf contained in the outflowing gas (yield %). Additionally, because HFC-245cb is a useful compound that can be converted into HFO-1234yf by dehydrofluorination, Table 1 also shows the selectivity for HFC-245cb in the "245cb" row.

TABLE 1

|  | Ex. 1 | Ex. 2 | Ex. 3 | Comp. Ex. 1 | Comp. Ex. 2 | Comp. Ex. 3 |
|---|---|---|---|---|---|---|
| Reaction Temperature (° C.) | 365 | 365 | 365 | 365 | 365 | 365 |
| Contact Time (W/F$_0$ g · sec/Nml) | 10 | 10 | 10 | 10 | 10 | 10 |
| Hydrogen Fluoride/Starting Material (Molar Ratio) | 40 | 40 | 32 | 10 | 10 | 15 |
| Type of Catalyst Degradation Inhibitor | None | Oxygen | Oxygen | None | Oxygen | Oxygen |
| Catalyst Degradation Inhibitor/Starting Material (Molar Ratio) | — | 0.1 | 0.1 | — | 0.1 | 0.1 |
| 1233xf Conversion (GC %) | 70 | 64 | 48 | 8 | 15 | 19 |
| Selectivity (Yield %) 1234yf | 61 | 63 | 71 | 70 | 70 | 72 |
| 245cb | 14 | 15 | 15 | 12 | 13 | 15 |
| Change in Conversion | −3% | −9% | −15% | −80% | −40% | −30% |

("Ex." indicates Example, and "Comp. Ex." indicates Comparative Example.)

As is clear from the results above, 30 moles or more of anhydrous hydrogen fluoride supplied to the reactor per mole of HCFO-1233xf supplied to the reactor was confirmed to be able to inhibit a change in conversion (reduction), while maintaining high conversion and selectivity. The results confirmed that 30 moles or more of anhydrous hydrogen fluoride supplied to the reactor per mole of HCFO-1233xf supplied to the reactor can inhibit degradation of a catalyst while maintaining high conversion and selectivity.

The invention claimed is:

1. A method for producing tetrafluoropropene represented by formula (1) CF$_3$CX=CHX
wherein Xs are different from each other and represent H or F,
the method comprising the step of bringing an organic substance containing monochlorotrifluoropropene represented by formula (2) CF$_3$CY=CHY wherein Ys are different from each other and represent H or Cl into contact with anhydrous hydrogen fluoride in the presence of a catalyst in a reactor,
wherein the amount of the anhydrous hydrogen fluoride supplied to the reactor is 30 moles or more per mole of the organic substance supplied to the reactor, and
the catalyst is at least one member selected from the group consisting of chromium oxide, aluminum oxide, magnesium oxide, cobalt oxide, chromium oxyfluoride, fluorinated alumina, magnesium oxyfluoride, cobalt oxyfluoride, nickel oxyfluoride, aluminum fluoride, magnesium fluoride, nickel fluoride, antimony fluoride, barium fluoride, antimony chloride, chlorofluoroantimony, and chlorofluorobarium.

2. The production method according to claim 1, wherein the amount of the anhydrous hydrogen fluoride supplied to the reactor is 30 to 100 moles per mole of the organic substance supplied to the reactor.

3. The production method according to claim 1, comprising supplying an oxidizing agent to the reactor.

4. The production method according to claim 3, wherein the amount of the oxidizing agent supplied to the reactor is 0.0001 to 0.5 moles per mole of the organic substance supplied to the reactor.

5. The production method according to claim 3, wherein the oxidizing agent is oxygen.

6. The production method according to claim 2, comprising supplying an oxidizing agent to the reactor.

7. The production method according to claim 6, wherein the amount of the oxidizing agent supplied to the reactor is 0.0001 to 0.5 moles per mole of the organic substance supplied to the reactor.

8. The production method according to claim 6, wherein the oxidizing agent is oxygen.

9. The production method according to claim 4, wherein the oxidizing agent is oxygen.

10. The production method according to claim 7, wherein the oxidizing agent is oxygen.

* * * * *